United States Patent
Ivie et al.

(10) Patent No.: US 9,670,479 B2
(45) Date of Patent: Jun. 6, 2017

(54) SAMPLE PREPARATION DEVICE AND METHODS OF USE

(71) Applicant: F Cubed, LLC, Hawthorn Woods, IL (US)

(72) Inventors: Leslie T. Ivie, Hawthorn Woods, IL (US); Christopher Chanelli, Hope Mills, NC (US); Shaunasee Kocen, South Bend, IN (US)

(73) Assignee: F CUBED, LLC, South Bend, IN (US)

( * ) Notice: Subject to any disclaimer, the term of this patent is extended or adjusted under 35 U.S.C. 154(b) by 580 days.

(21) Appl. No.: 14/216,746

(22) Filed: Mar. 17, 2014

(65) Prior Publication Data

US 2014/0272997 A1   Sep. 18, 2014

Related U.S. Application Data (60) Provisional application No. 61/791,766, filed on Mar. 15, 2013.

(51) Int. Cl.
| | | |
|---|---|---|
| C12N 15/10 | (2006.01) | |
| B01D 61/18 | (2006.01) | |
| B01D 63/08 | (2006.01) | |
| C12Q 1/68 | (2006.01) | |
| B01D 69/12 | (2006.01) | |
| B01D 71/50 | (2006.01) | |

(52) U.S. Cl.
CPC ......... *C12N 15/1017* (2013.01); *B01D 61/18* (2013.01); *B01D 63/087* (2013.01); *B01D 69/12* (2013.01); *B01D 71/50* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 5,057,426 A | 10/1991 | Henco et al. | |
| 5,591,841 A | 1/1997 | Ji et al. | |
| 5,652,141 A | 7/1997 | Henco et al. | |
| 5,836,905 A | 11/1998 | Lemelson et al. | |
| 5,938,904 A | 8/1999 | Bader et al. | |
| 6,136,555 A | 10/2000 | Jones | |
| 6,355,792 B1 | 3/2002 | Michelsen et al. | |
| 6,391,541 B1 | 5/2002 | Petersen et al. | |
| 6,455,287 B1 | 9/2002 | Jem | |
| 6,958,392 B2 | 10/2005 | Fomovskaia et al. | |
| 8,110,112 B2 | 2/2012 | Alburty et al. | |
| 8,187,476 B2 | 5/2012 | Dawson | |
| 2002/0106680 A1 | 8/2002 | Shinmyo et al. | |
| 2002/0197637 A1 | 12/2002 | Willson | |
| 2003/0175709 A1 | 9/2003 | Murphy et al. | |
| 2004/0132082 A1 | 7/2004 | Gautsch et al. | |
| 2004/0161767 A1 | 8/2004 | Baldwin et al. | |
| 2005/0115903 A1 | 6/2005 | Hallier-Soulier et al. | |
| 2006/0057738 A1 | 3/2006 | Hall, Jr. | |
| 2006/0134397 A1* | 6/2006 | Smith | B01D 67/0065 428/304.4 |
| 2006/0240448 A1 | 10/2006 | Bitner et al. | |
| 2008/0132694 A1 | 6/2008 | Himmelreich et al. | |
| 2008/0257071 A1 | 10/2008 | Wimberger et al. | |
| 2009/0042189 A1 | 2/2009 | Burns | |
| 2010/0021910 A1 | 1/2010 | Cao et al. | |
| 2010/0216220 A1* | 8/2010 | Dawson | G01N 30/6052 435/270 |
| 2010/0285578 A1 | 11/2010 | Selden et al. | |
| 2010/0331522 A1 | 12/2010 | Irvine et al. | |
| 2012/0252008 A1 | 10/2012 | Brown et al. | |
| 2013/0040376 A1 | 2/2013 | Amshey et al. | |
| 2013/0264266 A1* | 10/2013 | Shick | A61M 5/165 210/236 |

FOREIGN PATENT DOCUMENTS

| | | |
|---|---|---|
| EP | 0268946 B1 | 6/1988 |
| EP | 0755401 B1 | 1/1997 |
| EP | 1367137 B1 | 3/2010 |
| WO | WO03072718 A2 | 9/2003 |
| WO | WO2011019428 A2 | 2/2011 |
| WO | WO2012002887 A1 | 1/2012 |
| WO | WO2013013687 A1 | 1/2013 |
| WO | WO2013029919 A1 | 3/2013 |

OTHER PUBLICATIONS

Pall, Acrodisc® PSF Syringe Filters Expedite Automated Sample Processing, attached, available at https://www.pall.com/main/laboratory/acrodiscpsfsyringefiltersexpediteau39544.page, Sep. 30, 2011.*

Kuo, Tai-Chih "Streamlined method for purifying single-stranded DNA from PCR products for frequent or high-throughput needs", BioTechniques, vol. 38, No. 5, 2005, pp. 700-702.

MagMAX Total Nucleic Acid Isolation Kit; http://www.thermofisher.com/order/catalog/product/AM1840.

Molecular Biology: Working with DNA Polymerase Chain Reaction—Asymmetric PCR and Single Sided PCR; Center for Cocoa Biotechnology Research and Development, www.koko.gov.my/CocoaBioTech/PCRxn3.html.

Tang, X., et al. Simple and effective method for generating single-stranded DNR targets and probes. BioTechniques 40: 759-763 (Jun. 2006).

Triant, Deborah A., et al. "Simultaneous Extraction of High-Quality RNA and DNA from Small Tissue Samples", Journal of Heredity 2009: 100(2): 246-250.

Wilson, Robert "Preparation of Single-Stranded DNA from PCR Products with Streptavidin Magentic Beads", Nucleic Acid Ther. Dec. 2011; 21(6): pp. 437-440.

* cited by examiner

*Primary Examiner* — Aaron Priest
(74) *Attorney, Agent, or Firm* — Honigman Miller Schwartz and Cohn LLP; Douglas H Siegel; Andrew S. Chipouras (57) ABSTRACT

A device for isolating DNA from a sample containing cells, including a cartridge having an entrance port and an exit port, a membrane disposed between the entrance port and the exit port, and a plurality of channels between the membrane and the exit port. Additionally, systems and methods for isolating DNA from a sample containing cells and also systems and methods for amplifying and isolating single-stranded DNA from a sample containing DNA.

35 Claims, 11 Drawing Sheets

SAMPLE PREPARATION DEVICE AND METHODS OF USE

CROSS-REFERENCE TO RELATED APPLICATIONS

This U.S. patent application claims priority to U.S. Provisional Application 61/791,766 filed on Mar. 15, 2013, the disclosure of which is considered part of the disclosure of this application and is hereby incorporated by reference in its entirety.

FIELD OF THE INVENTION

The present invention relates to novel devices, systems, and methods for isolating DNA from a sample containing cells.

BACKGROUND

Isolating DNA from a sample is important for many diagnostic applications. DNA detection is utilized for diagnostic applications in medicine, food safety, environmental testing, and forensic science. Isolated DNA may be analyzed using methods such as polymerase chain reaction (PCR), electron microscopy, Western blotting, or other techniques. Isolating single-stranded DNA (ssDNA) is of particular importance in diagnostic applications where detection is based on hybridization of the ssDNA with a DNA probe. In samples containing a relatively low number of cells, DNA amplification may also be desirable to produce a detectable level of DNA.

Current techniques for DNA isolation involve the use of a membrane or filter to trap DNA after a cell is lysed to release DNA from the cell. This trapping is often followed by elution of the DNA from the membrane using an elution buffer. Such methods can be time consuming, requiring multiple washing and elution steps. In some cases, such methods may result in a low yield of DNA. In some cases, the DNA isolation systems may not be suitable for point-of-care use. Some methods may have a sample output that is unsuitable for integration with functions such as DNA amplification and DNA detection assays. For example, if the sample output is contaminated with non-DNA cellular material the efficiency of downstream functions is reduced. Other disadvantages in known methods include a lack of support for the membrane. This may result in tearing of the membrane, wherein pieces of the membrane may contaminate the sample.

SUMMARY OF THE INVENTION

One aspect of the invention is a device for isolating DNA from a sample containing cells, comprising a cartridge having an entrance port and an exit port; a membrane disposed between the entrance port and the exit port; and a plurality of channels between the membrane and the exit port.

Another aspect of the invention is a method of isolating DNA from a sample, comprising providing a sample containing cells; transferring the sample into a container ("cartridge") having a membrane and a plurality of channels disposed therein; lysing the cells to release their DNA and other (non-DNA) cellular material from the cell; and passing the released DNA through the membrane and through the channels.

Another aspect of the invention is a system for isolating single-stranded DNA from a sample containing cells, comprising a container ("cartridge") having an entrance port and an exit port; a membrane disposed within the container between the entrance port and the exit port; and a plurality of channels located between the membrane and the exit port; and an amplification and separation system comprising an amplification container; a thermal cycler; and a magnetic substrate.

Another aspect of the invention is a method of isolating single-stranded DNA from a sample, comprising providing a sample containing cells; transferring the sample into a container ("cartridge") having a membrane and a plurality of channels disposed therein; lysing the cells to release the DNA and non-DNA cellular material from the cell; passing the DNA through the membrane and the channels; transferring the released DNA to an amplification container, amplifying the released DNA via a polymerase chain reaction (PCR) to produce double-stranded DNA and single-stranded DNA; and separating the double-stranded DNA from the single-stranded DNA by applying a magnetic field.

In some embodiments the PCR includes asymmetric PCR to produce single-stranded DNA (ssDNA). In another aspect a magnetic substrate with binding affinity for double-stranded DNA (dsDNA) is provided and a magnetic field is applied to the substrate to isolate the ssDNA.

BRIEF DESCRIPTION OF THE DRAWINGS

The disclosure will now be described, by way of example, with reference to the accompanying drawings in which.

DETAILED DESCRIPTION

As used herein, the following definitions shall apply unless otherwise indicated.

I. Definitions

As used herein, "DNA" refers to the polymeric form of deoxyribonucleotides (adenine, guanine, thymine, or cytosine) in its either single-stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

As used herein "ssDNA" refers to single-stranded DNA and "dsDNA" refers to double-stranded DNA.

As used herein, "isolating" refers to separating a first component from other components and includes partial separation wherein the first component is not totally separated from the other components and impurities of the other components remain. Isolating may be thought of as concentrating the first component relative to other components.

As used herein, "cartridge" refers to a container.

As used herein, "channel" or refers to an opening defined by boundary walls.

As used herein, "cellular homogenizer" refers to a mechanical device capable of shaking an object, for example the cartridge described herein. For example, a cellular homogenizer may be capable of shaking an object at a speed of up to about 5000 rpm.

As used herein, "PCR" refers to polymerase chain reaction. "Asymmetric PCR" (APCR) is a form of PCR that preferentially amplifies one strand of a target dsDNA. It is to generate an ssDNA as product. Thermocycling is carried out as in traditional PCR, but with APCR (as compared to traditional PCR) an excess of the primer for the strand targeted for amplification is used, or a limiting amount of one of the other primers is used or is absent. When the limiting primer becomes depleted, replication increases arithmetically through extension of the excess primer.

As used herein, "thermal cycler" refers to an apparatus configured to manipulate temperature. For example a thermal cycler may be configured to manipulate the temperature of a liquid sample. A thermal cycler may be configured to cycle a sample between various temperatures for a desired PCR protocol.

II. Devices and Systems

Cartridge Product

Figure 1:
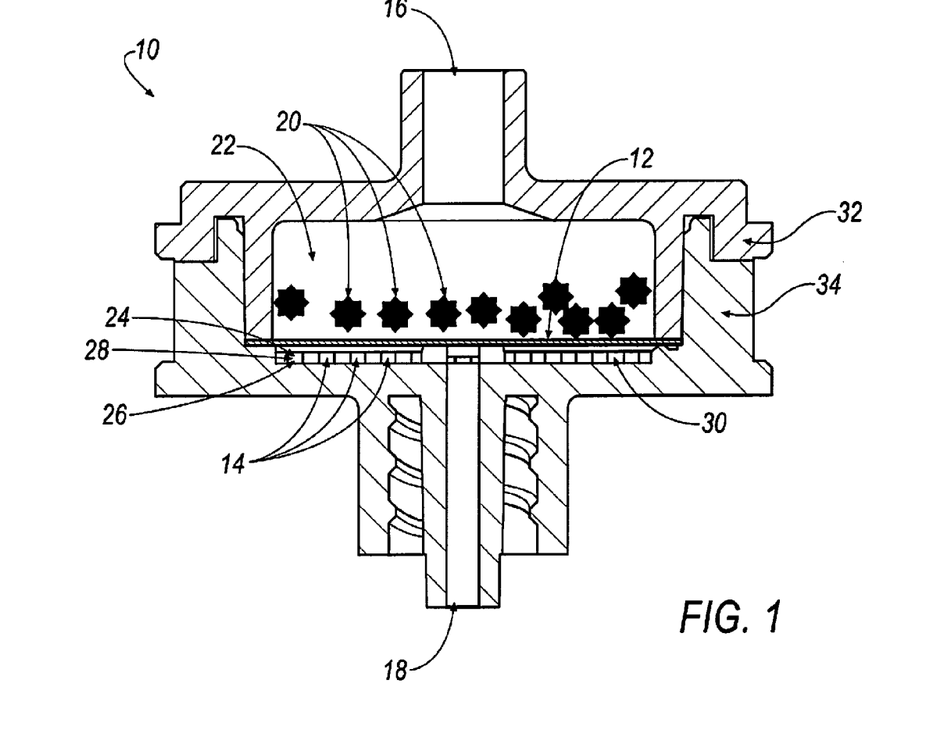
FIG. 1 presents a cross-sectional view of an embodiment of a device for isolating DNA from a sample containing cells.
Figure 2:
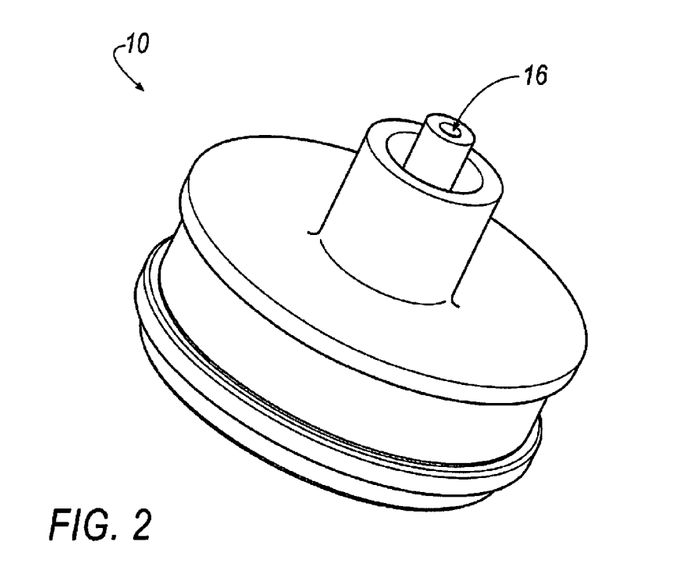
FIG. 2 presents an outer perspective view of an embodiment of a device for isolating DNA from a sample containing cells.
Figure 3:
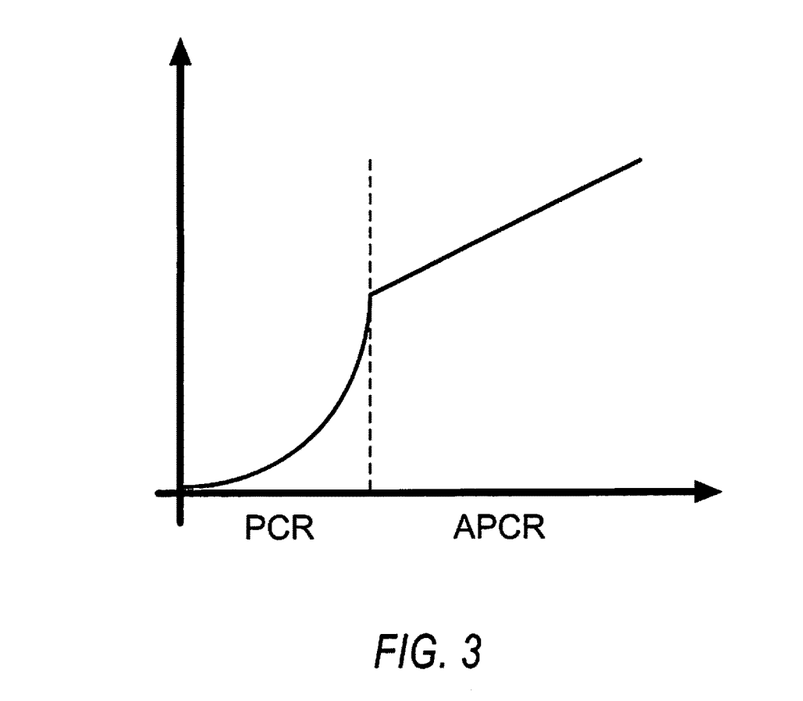
FIG. 3 is a graph illustrating the theoretical production of DNA over time for traditional PCR followed by asymmetric PCR (APCR).

One aspect of the invention is a device for isolating DNA from a sample containing cells, comprising a container 10 having an entrance port 16 and an exit port 18; a membrane 12 disposed between the entrance port 16 and the exit port 18; and a plurality of channels 14 between the membrane 12 and the exit port 18.

In one embodiment of the present invention, the channels 14 are adjacent to the membrane 12.

In another embodiment, each channel 14 has a channel entrance 24, a channel exit 26, wherein the channel entrance 24 is adjacent to the membrane 12.

In a further embodiment, the channels 14 are substantially linear channels with the channel entrance 24 adjacent to the membrane 12 and the channel extending linearly from the channel entrance 24 to the channel exit 26 in a direction substantially perpendicular to the adjacent membrane surface or in a direction generally towards the exit port 18 of the cartridge 10. In some embodiments the substantially linear channels are substantially parallel to one another. In some embodiments the channels 14 are curved or bent channels with the channel entrance 24 adjacent to the membrane 12 and the channel exit 26 extending toward the exit port 18 of the cartridge 10 and to support the membrane 12.

In some embodiments the plurality of channels 14 are arranged in a matrix. For example the channels 14 form a grid-like matrix or the channels 14 may form a matrix extending radially outward from a center point. In some embodiments the channels 14 are directly adjacent to each other or alternatively the channels 14 may be spaced apart from each other. In some embodiments the matrix of channels 14 further comprises a solid barrier 30 between the entrances 24 of each channel to direct the flow through the channels.

In one embodiment, the device has from about 2 to about 1000 channels 14, for example, from about 10 to about 100 channels 14.

In some embodiments the dimensions of the channels 14 are selected to optimize the flow of DNA out of the cartridge 10. For example the channels 14 have a dimension of their cross-section that results in a minimal number of DNA being held in the channels 14. For example, the channels have at least one dimension that is from about 0.1 mm to about 10 mm. For example the width of the cross section of the channels is from about 0.1 mm to about 10 mm and the length of the cross section of the channels is from about 0.1 mm to about 100 mm.

Without being bound by theory, it is believed that channels with too large of a dimension can result in DNA being held at the walls of the channels without being carried by the flow of liquid through the channel and out of the cartridge. In some embodiments the channels 14 have at least one dimension that is from about 0.1 mm to about 10 mm so that the amount of DNA held at the channel walls 28 is minimized. Without being bound by theory, it is believed that channels with too small of a dimension can result in DNA blocking flow through the channels or can result in irregular flow patterns that keep DNA from being carried by the flow of liquid through the channel. In one embodiment, the channels 14 have at least one dimension that is from about 0.1 mm to about 10 mm so that the amount of DNA blocking the channel is minimized. In some embodiments the channels have at least one dimension that is from about 0.1 mm to about 10 mm so that the amount of irregular flow patterns is minimized In some embodiments each channel entrance 24 is substantially rectangular and has a length and a width. In some embodiments the channel entrance 24 has a length of about 0.1 mm to about 100 mm and a width of about 0.1 mm to about 10 mm.

Alternatively, each channel entrance 24 may be substantially circular and have a diameter. In some embodiments the channel entrance 24 has a diameter of about 0.1 mm to about 10 mm.

In some embodiments the channels 14 and/or channel entrances 24 form a concentric pattern around a central axis of the cartridge. For example FIG. 9B shows concentric channels around a central axis of the cartridge.

In some embodiments the channels 14 have a substantially consistent cross section across their entire length. In some embodiments the cross section varies across the length of the channel 14. For example the cross section at the channel entrance 24 has a smaller area than the cross section at the channel exit 26.

In some embodiments each of the channels 14 have substantially the same cross section or cross section profile as one another. In other embodiments the cross section varies from one channel 14 to another.

In some embodiments the channels 14 have a depth of about 0.1 mm to about 10 mm, for example about 0.5 mm.

In some embodiments the membrane 12 is made from a cellulose material. For example the membrane comprises cellulose nitrate or cellulose acetate 12. In some embodiments the membrane comprises a polycarbonate material 12. In some embodiments the membrane comprises a membrane material known in the art for use in isolating DNA from cells.

In some embodiments the membrane 12 is a layered membrane. For example the membrane 12 has two or more layers, e.g., three or more layers.

In some embodiments the membrane 12 has pores. The pore size may be about 10 nm to 1 micron. For example, the membrane 12 has a pore size of from about 100 nm to about 300 nm, e.g., about 200 nm. The pore size is selected to maximize the yield of DNA passing through the membrane 12 and to minimize the amount of cells and non-DNA cellular material that can pass through the membrane 12.

The membrane 12 may be configured to be permeable to DNA but substantially impermeable to cells. In some embodiments, the membrane 12 is configured to be permeable to DNA but substantially impermeable to "non-DNA cellular material" (i.e., cellular debris), which includes, but is not limited to, material other than DNA released form a lysed cell such as proteins, cell walls, and organelles. The membrane 12 is permeable to DNA when, for example, 50%, 60%, 70%, 80%, 90%, 95%, or 99% or more of the DNA released from the cells flows through the membrane. In some embodiments, membrane 12 is substantially impermeable to non-DNA cellular material when, for example 50%, 60%, 70%, 80%, 90%, 95%, or 99% or more of the non-DNA cellular material does not flow through the membrane. Similarly, membrane 12 is substantially impermeable to cells when, for example 50%, 60%, 70%, 80%, 90%, 95%, or 99% or more of the cells do not flow through the membrane.

In some embodiments the membrane 12 allows particulates smaller than about 100 nm to about 1000 nm to pass through but is impermeable to particulates larger than about 100 nm to about 1000 nm. For example the membrane 12 allows particulates smaller than about 200 nm to pass through but not particulates larger than about 200 nm. It may be possible from some non-DNA cellular material having a size approximately equal to or smaller than DNA ("minor cellular debris") to pass through the membrane 12, however such minor cellular debris has a minimal effect on downstream applications.

In some embodiments the device further comprises a plurality of particulate material 20, (e.g. beads), within the cartridge 10, located between the membrane 12 and the entrance port 16. In some embodiments the space located between the membrane 12 and the entrance port 16 defines a lysis chamber 22.

In some embodiments the particulate material 20 is a plurality of microbeads. The microbeads may be substantially spherical. In some embodiments the particulate material 20 comprises a ceramic material (e.g., glass) or a metal material (e.g. stainless steel). For example, the particulate material 20 is glass microbeads or stainless steel microbeads. In some embodiments the microbeads have a diameter of from about 10 micron to about 1000 microns, for example about 200 to 400 microns.

In some embodiments the entrance port 16 and exit port 18 include standard luer lock fittings 17 and 19.

Figure 7:
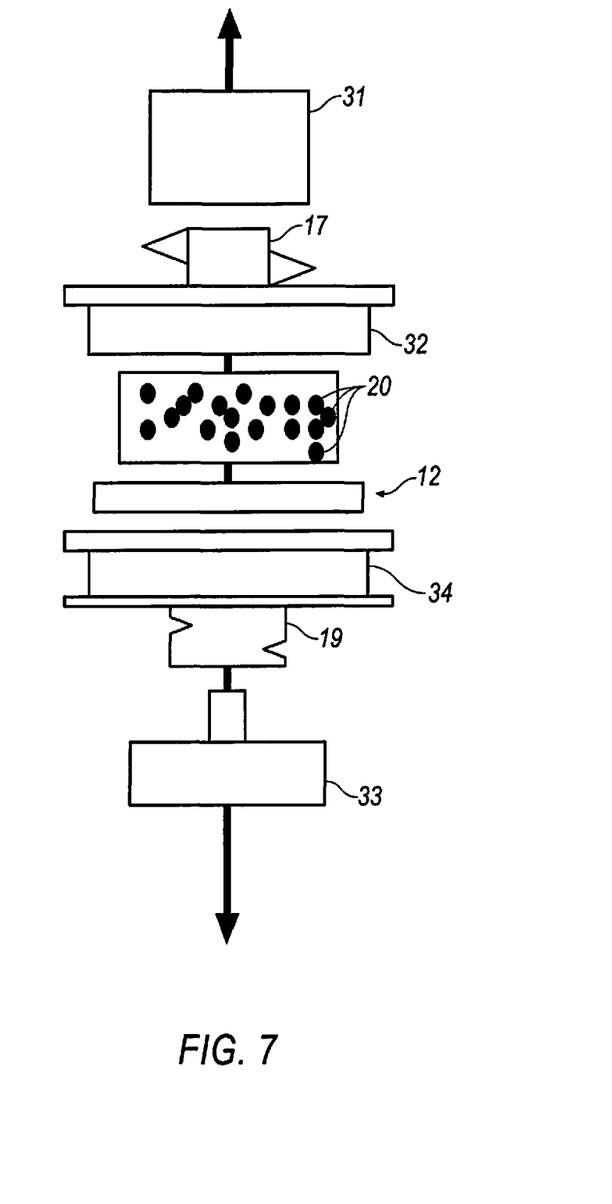
FIG. 7 presents an example of components used in the manufacture of an embodiment of a device for isolating DNA from a sample containing cells (e.g., a cartridge).

The cartridge 10 may include an top piece, referred to as a top SPC (sample prep cartridge) 32 and a bottom piece, referred to as a bottom SPC 34. In some embodiments the cartridge is made of a plastic material, e.g. polypropylene.

In some embodiments the top SPC 32 and bottom SPC 34 are sealed together, e.g., the top SPC 32 and bottom SPC 34 are sonic welded together. In this embodiment the membrane 12 is held in place by the top SPC 32 and bottom SPC 34. For example, the membrane 12 is located between the top SPC 32 and bottom SPC 34 and held in place when the top SPC 32 and bottom SPC 34 are sealed together. In some embodiments the edges of the membrane 12 are stretched into place at the sealed boundary of the top SPC 32 and bottom SPC 34.

In some embodiments the channels 14 are disposed within the bottom SPC 34. For example the channels 14 are defined as cavities within the bottom SPC 34 and the channels 14 allow for flow of DNA and liquid through the membrane 12 and out of the cartridge 10 through the exit port 18. In some embodiments the membrane is positioned across a channel matrix, wherein the channel matrix is defined as a plurality of cavities in the bottom SPC 34.

In some embodiments the bottom SPC 34 and the channel matrix act as a support for the membrane 12 while allowing for the flow of liquid out of the cartridge 10. For example, the membrane 12 is held in place by the seal of the top SPC 32 and the bottom SPC 34 and is supported by an inner surface of the bottom SPC 34 while still allowing for flow through the membrane 12 and out of the cartridge 10 due to flow path provided by the channels 14. In some embodiments the support provided to the membrane 12 results in the membrane 12 remaining intact during use, for example, during mechanical lysis. In some embodiments the membrane 12 remaining intact has the advantage of avoiding contamination of the sample. For example the membrane 12 remains intact while being shaken by a cellular homogenizer wherein particulate material 20 is agitated within the cartridge 10 and contacts the membrane 12.

Integrated System

Figure 4:
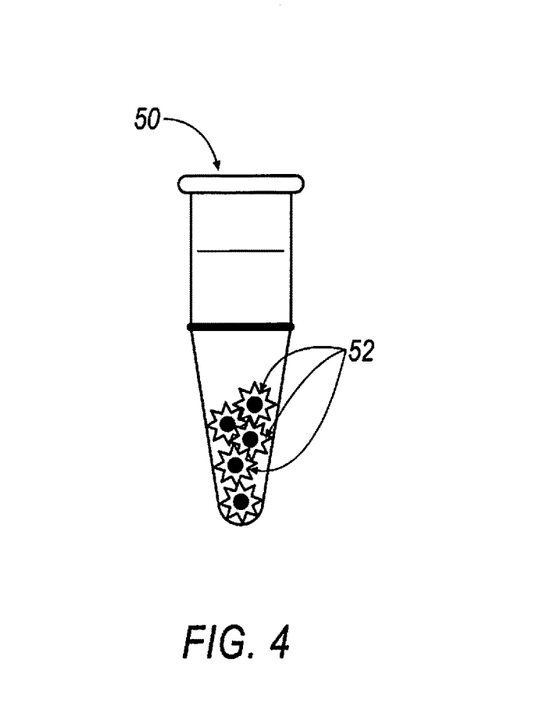
FIG. 4 presents a cross-sectional view of an embodiment of an amplification container with a magnetic substrate.
Figure 5:
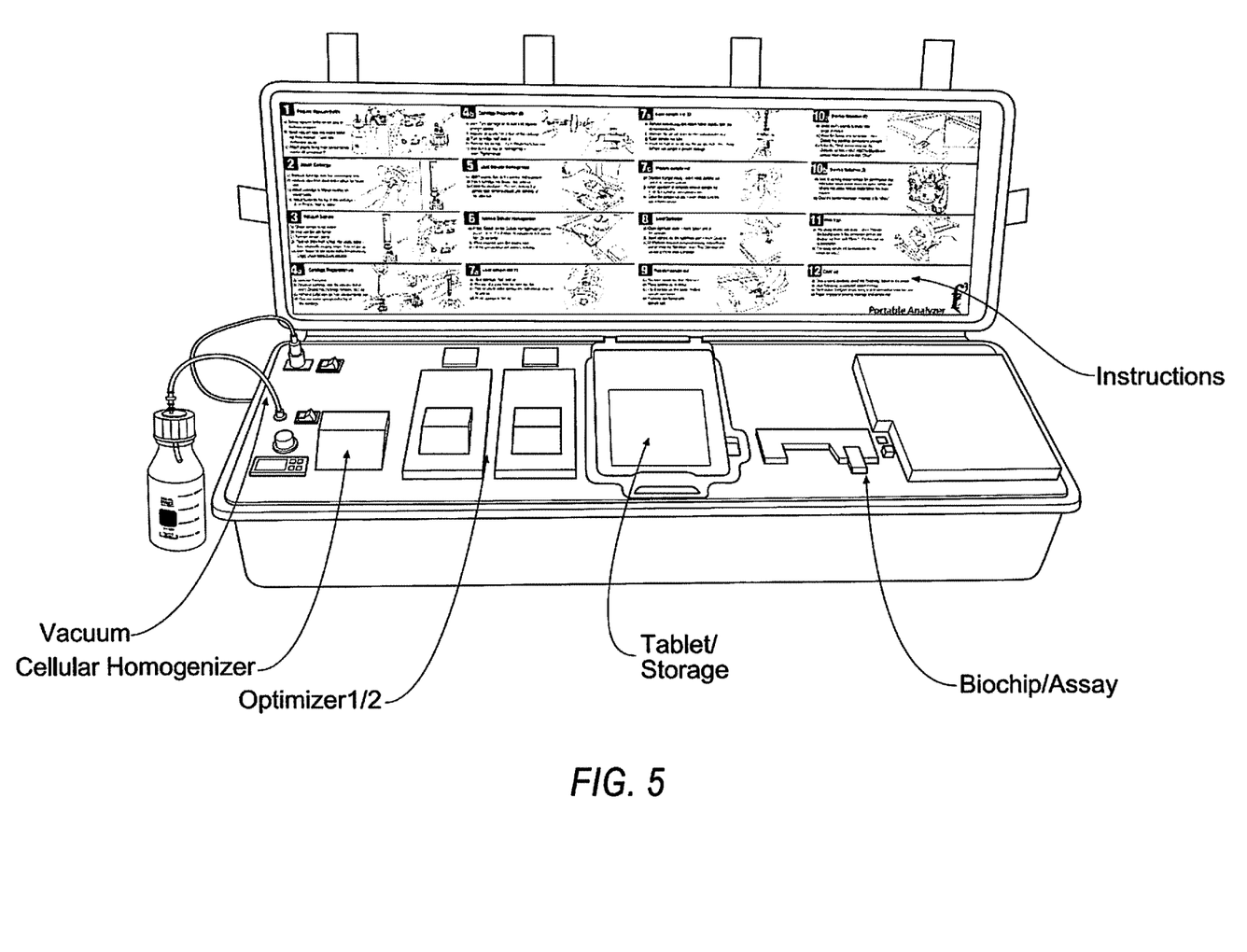
FIG. 5 presents an embodiment of a system for isolating single-stranded DNA from a sample containing cells.

Another aspect of the invention is a system for isolating single-stranded DNA from a sample containing cells, comprising: a container 10 having an entrance port 16 and an exit port 18, a membrane 12 disposed within the container 10 between the entrance 16 port and the exit port 18, and a plurality of channels 14 located between the membrane 12 and the exit port 18; and an amplification and separation system comprising an amplification container 50, a thermal cycler, and a magnetic substrate 52.

In some embodiments the system integrates a device for isolating DNA from a sample containing cells, as described hereinabove, with a system for amplification and separation to amplify and isolate single-stranded DNA.

The system also may include pumps, valves, channels, tubes, fittings, syringes, chambers, containers, and/or vacuum sources to transfer a sample containing cells into and out of the cartridge 10 and into and out of an amplification container 50. For example, the system is configured to flow an initial sample containing cells suspended in a liquid into the cartridge 10 and remove the liquid from the cells by passing the liquid through the membrane 12 and channels 14 and out the exit port 18 of the cartridge 10 leaving cells (and non-DNA cellular material) trapped on the membrane 12. In some embodiments the cells trapped on the membrane within the cartridge are re-suspended in a liquid, for example, a buffer. In some embodiments the system is configured to re-suspend the cells trapped on the membrane in a small volume of liquid to increase the concentration of DNA per volume and improve downstream applications.

In one embodiment the system further comprises a vacuum configured to pull a liquid sample containing cells through the cartridge 10 wherein the cells are trapped on the membrane 12 and the liquid is removed from the cartridge 10. The system may also include a syringe containing a liquid sample configured to be attached to the entrance port 16.

In some embodiments the cartridge is sized and configured to fit within a cellular homogenizer capable of shaking the cartridge 10 to agitate the particulate material 20 (e.g., microbeads) within the lysis chamber 22. For example, the cellular homogenizer can shake the cartridge at speeds up to about 5000 rpm.

In some embodiments the amplification and separation system comprises the amplification container 50 for amplifying DNA via PCR. In some embodiments the amplification container 50 is sealed to hold in moisture during PCR. For example, the amplification container 50 includes a wax seal at a lid of the container to hold in moisture during PCR, wherein the wax seal melts to seal the lid of the amplification container 50. In some embodiments the amplification container 50 is a plastic tube, for example, a microcentrifuge tube. In one embodiment, the amplification container 50 can hold a volume of liquid of up to about 1 or 2 mL.

A thermal cycler may be included to control the temperature within the amplification container 50. In some embodiments the thermal cycler is programmed to subject the container to predetermined PCR thermal cycles. For example the thermal cycler is programmed to subject the container to a plurality of thermal cycles for PCR followed by a plurality of cycles for asymmetric PCR.

In some embodiments the amplification container 50 is loaded with PCR reagents. For example, the amplification container is loaded with primers, enzymes (DNA polymerase), and nucleotides and/or other PCR components and reagents known in the art. For example the amplification container is loaded with reagents such that the reagents are optimized to undergo PCR followed by asymmetric PCR. In some embodiments asymmetric PCR is used to generate single-stranded DNA. More specifically, asymmetric PCR may be used to generate single-stranded DNA of a specific length or within a specific range of lengths, for example ssDNA of from about 10 to about 200 bases or, for example, less than 100 bases.

In another embodiment, the amplification container 50 contains magnetic substrate 52, such as magnetic beads. In some embodiments the magnetic beads are silica-based beads. In one example the magnetic beads are paramagnetic beads. In some embodiments the magnetic substrate 52 is a plurality of substantially spherical beads of about 1 micron to about 100 microns, for example about 10 microns in diameter.

In some embodiments the magnetic substrate 52 includes a coating that is capable of attracting double-stranded DNA but does not substantially attract single-stranded DNA. In some embodiments the coating has a binding affinity for double-stranded DNA that is greater than its binding affinity for single-stranded DNA. In some embodiments the coating decreases the time for elongating ssDNA during asymmetric PCR. In some embodiments the coating comprises a carboxylic acid linker. In some embodiments the coating comprises N-hydroxysuccinamide (NHS).

In some embodiments the amplification and separation system further includes a magnet configured to apply a magnetic field to the magnetic substrate. For example, the magnet is positioned underneath the amplification container. The magnet may be a paramagnet.

In some embodiments the systems are small, portable, and inexpensive relative to known systems.

III. Methods

Another aspect of the invention is a method of isolating DNA from a sample, comprising providing a sample containing cells (i.e., any biological sample that includes cells); transferring the sample into a container having a membrane and a plurality of channels disposed therein; lysing the cells to release DNA and non-DNA cellular material; passing DNA through the membrane; and passing the DNA through the channels.

In some embodiments, the sample containing cells is a liquid sample. For example the sample comprises blood, urine, water, or exudate.

The cells in the sample may be any cells that include DNA, for example, bacteria. Exemplary cells include *E. coli, Listeria, Brucella*, MRSA and *Enterococcus*. In some embodiments the DNA is isolated from a blood or urine sample from a patient being tested for a disease, for example, lymphatic filariasis or dengue fever.

In one embodiment, the sample is transferred into the cartridge 10 (e.g. as described above) using a vacuum. In another embodiment, the sample is transferred into the cartridge using a pump.

More specifically, for example, a liquid sample is drawn or pushed into the cartridge 10 and the cells are trapped on membrane 12, while the liquid flows through the membrane 12 and channels 14 and exits the cartridge 10 and is collected as waste.

In some embodiments a liquid, e.g. a buffer, is pushed or drawn into the cartridge 10 and the cells trapped on the membrane 12 are re-suspended in the liquid. The liquid may be selected from water, a buffer such as a lysis buffer, saline buffer, mild ionic buffer, or strong ionic buffer. The buffer can be selected on the basis of its interaction with cells (e.g., lysis buffer, isotonic buffer), its interaction with DNA (e.g., hybridization buffer), its effect on the interaction of cells and DNA with the membrane (e.g., an elution buffer) or its suitability for downstream applications such as amplification or detection methods (e.g. PCR buffer, hybridization buffer, high or low conductivity buffer). In one embodiment, the buffer is phosphate-buffered saline (PBS).

Another step of the inventive method may include re-suspending the DNA only once while it pushed through the cartridge 10 to be isolated. For example, the DNA does not undergo multiple washing and elution steps. In some embodiments the DNA is suspended in a small volume of buffer (e.g. less than 100 mL in order to concentrate the DNA and allow for more efficient downstream functions).

Using the present method the cells are trapped within lysis chamber 22, a region between the entrance port 16 and the membrane 12. In some embodiments the cells are lysed within the lysis chamber 22. In other embodiments, the cells are lysed prior to being transferred to the cartridge 10.

The cells may be lysed by chemical, mechanical, thermal, or electrical means. For example, the cells are lysed using a lysis buffer such as tris-HCl, EDTA, EGTA, SDS, deoxycholate, triton, NP-40 and/or a buffer containing NaCl or the cells may be lysed by heating the cells. The cells may also be lysed by mechanical means such as bead beating, shear forces, gas bubble agitation, or sonication.

In some embodiments the cells are mechanically lysed using particulate material 20 (e.g. beads or microbeads), contained within lysis chamber 22. For example a cellular homogenizer shakes cartridge 10 to agitate particulate material 20 and the cells within the cartridge 10. The purpose of the particulate material 20 is to rupture the cell membranes or walls of the cells and release DNA. In one embodiment, the beads are glass microbeads or stainless steel microbeads. During use, the cellular homogenizer shakes cartridge 10, e.g., at a rate of about 3000 rpm. The non-DNA cellular material may be substantially destroyed leaving biohazard free waste. In some embodiments, the cellular homogenizer shakes cartridge 10 for about 60 to about 300 s. The non-DNA cellular material is substantially destroyed when, for example 50%, 60%, 70%, 80%, 90%, 95%, or 99% or more of the non-DNA cellular material is destroyed.

In some embodiments the DNA released from the cells flows through membrane 12. For example, 50%, 60%, 70%, 80%, 90%, 95%, or 99% or more of the DNA released from the cells flows through membrane 12. In some embodiments the non-DNA cellular material does not flow through membrane 12. For example 50%, 60%, 70%, 80%, 90%, 95%, or 99% or more of the non-DNA cellular material does not flow through membrane 12.

In some embodiments the released DNA that flows through membrane 12 subsequently flows through channels 14. For example 50%, 60%, 70%, 80%, 90%, 95%, or 99% or more of the DNA that flows through membrane 12 will then flow through channels 14. In some embodiments the yield of DNA isolated from the sample is greater than 50%, 60%, 70%, 80%, 90%, 95%, or 99%.

In some embodiments the DNA that flows through channels 14 flows out exit port 18 of cartridge 10. The DNA may be suspended in liquid, e.g. buffer, and the suspension is collected. For example, the suspension is collected and transferred to a downstream application, such an amplification or detection function. In some embodiments the DNA is pushed with a dry syringe (air) into a separate container for downstream applications.

Another aspect of the invention is a method of amplifying and isolating single-stranded DNA from a sample containing DNA, comprising providing a sample containing DNA; amplifying the DNA via a polymerase chain reaction (PCR), wherein the PCR includes asymmetric PCR, and wherein the PCR produces a mixture comprising double-stranded DNA and single-stranded DNA; providing a magnetic substrate 52, wherein the magnetic substrate 52 has an affinity for binding double-stranded DNA; applying a magnetic field to the magnetic substrate 52; and isolating the unbound single-stranded DNA from the sample.

Another aspect of the invention provides combining the method of isolating DNA from a sample containing cells, as described herein, with the method of amplifying and isolating single-stranded DNA from a sample containing DNA, as described herein, such that an initial sample containing cells is processed to produce a sample comprising isolated single-stranded DNA.

In some embodiments the amplification comprises traditional PCR followed by asymmetric PCR. In some embodiments the traditional PCR followed by asymmetric PCR produces a mixture of double-stranded DNA and single-stranded DNA. This protocol may produce a portion of the ssDNA within a specified range of lengths. For example, a portion of the ssDNA is approximately 50 to 200 bases in length or a portion of the ssDNA is approximately 100 bases in length. For example the concentration of ssDNA within a specified range of lengths is greater than about 100 nM. For example the concentration of ssDNA with a length of 50 to 200 bases or a length of approximately 100 bases, is greater than about 100 nM.

In some embodiments, the mixture of dsDNA and ssDNA undergoes a separation procedure to separate the ssDNA from the dsDNA. In one embodiment the dsDNA is bound to magnetic substrate 52, for example, a plurality of magnetic beads. In this embodiment, the dsDNA is attracted to a coating on the magnetic beads and binds to the coating on the magnetic beads. The magnetic substrate 52 may comprise a carboxylic acid linker. In some embodiments the magnetic substrate also functions to elongate ssDNA during asymmetric PCR.

In some embodiments, greater than 50%, 60%, 70%, 80%, 90%, 95%, or 99% of the dsDNA in the mixture is bound to the magnetic substrate 52 and, respectively, less than 50%, 40%, 30%, 20%, 10%, 5%, or 1% of the dsDNA in the mixture is not bound to the magnetic substrate 52. In other embodiments, greater than 50%, 60%, 70%, 80%, 90%, 95%, or 99% of the ssDNA in the mixture is recovered from the mixture. ssDNA isolated by this process may be used in downstream applications, for example, in a detection assay based on hybridization of the ssDNA with a specific DNA probe. In some embodiments, the unbound ssDNA is isolated from the mixture. For example, liquid is slowly drawn from the sample, while the magnetic beads bound to the dsDNA remain held by the magnet. In some embodiments, the isolated unbound ssDNA as compared to the unbound and bound dsDNA comprises a ratio of greater than 50:50, 60:40, 70:30, 80:20, 90:10, 95:5, 99:1 of unbound ssDNA to unbound/bound dsDNA. In one example, this ratio is 100:1 and in another example 1000:1 of unbound ssDNA to unbound/bound dsDNA.

In some embodiments the methods can be performed in a reduced time compared to known methods, and/or with reduced technician time required to carry out the process. In some embodiments the methods do not require multiple steps, such as washing and elution steps. In some embodiments the methods result in a high yield of DNA and/or single-stranded DNA.

IV. EXAMPLES

In order that the invention described herein may be more fully understood, the following examples are set forth. It should be understood that these examples are for illustrative purposes only and are not to be construed as limiting this invention in any manner.

Example No. 1: Process Protocol

With reference to FIGS. 6A, 6B, 6C, and 6D an example protocol is described. A vacuum bottle (or "waste bottle") is set up where one end of a vacuum tube is inserted into a cap hole in the vacuum bottle and the other end of the vacuum tube is inserted into a vacuum source. A plastic fitting is inserted into a second cap hole. See, FIGS. 6A(i)-6A(iii).

A cartridge is attached to the fitting on the second cap hole of the vacuum bottle. A funnel is attached to the top of the cartridge using the luer lock fittings. See, FIGS. 6A(iv)-6A(v).

A sample containing cells with a volume of about 5 to 100 mL is obtained and transferred into the funnel. The vacuum pump is activated and fluid is drawn from the funnel, through cartridge 10, and into the vacuum bottle. The cells in the sample are trapped on membrane 12 (not shown) within cartridge 10. See, FIGS. 6A(vi)-6A(vii).

The funnel is removed from cartridge 10 and cartridge 10 is removed from the fitting on the cap of the vacuum bottle. A buffer syringe with PBS buffer is attached to the top of cartridge 10. See, FIGS. 6A(viii)-6A(x). The buffer syringe is attached to cartridge 10 and buffer is slowly pushed into cartridge 10 at a flow rate of about 0.5 to 4 mL/s. The volume of buffer pushed into cartridge 10 is from about 10 mL to about 30 mL. Cartridge 10 is closed with caps on entrance port 16 and exit port 18. The process time for the steps above is from about 15 to about 120 seconds. See, FIGS. 6B(i)-6B(ii).

Cartridge 10 is placed inside a cellular homogenizer. See, FIG. 6B(iii). The cellular homogenizer is activated and shakes cartridge 10. See, FIG. 6B(iv). The cellular homogenizer operates for 60 to 300 seconds at a speed of about 1000 to 3500 rpm. The cellular homogenizer is then deactivated and cartridge 10 is removed.

An empty (air) syringe is attached to entrance port 16 of cartridge 10 and a needle is attached to exit port 18. See, FIG. 6B(v) and FIG. 6C(i). The syringe is slowly depressed to push the liquid inside cartridge 10 through membrane 12 and channels 14 and into a sample vial. See FIG. 6C(ii). The sample vial is prefilled with magnetic substrate 52 and PCR reagents. Forms of magnetic substrate 52 are commercially available, e.g., magnetic beads such as PureProteome NHS Flexibind Magnetic Beads, Millipore product number LSK-MAGNXXMAN. The PCR reagents are commercially available, GE Healthcare Illustra PuRe Taq Ready-to-Go PCR. Primers are specially designed for the desired assay. Commercially available primers may be made by IDTDNA.

The sample vial is loaded into a thermal cycler (optimizer). See FIG. 6C(iii). The DNA in the sample vial undergoes PCR followed by asymmetric PCR for about 20-45 minutes in the optimizer. PCR includes a ramp up to 90-98 degrees Centigrade for 2 minutes. 18-30 total cycles of PCR and asymmetric PCR amplify the DNA. The cycles include a hot step at 90-98 degrees Centigrade for 10-20 seconds, a cool step at 55-65 degrees Centigrade for 15-25 seconds, and a copy step at 70-75 degrees Centigrade for 25-35 seconds. The sample undergoes a final cool down step at 70-75 degrees Centigrade for 3 min.

Figure 6A:
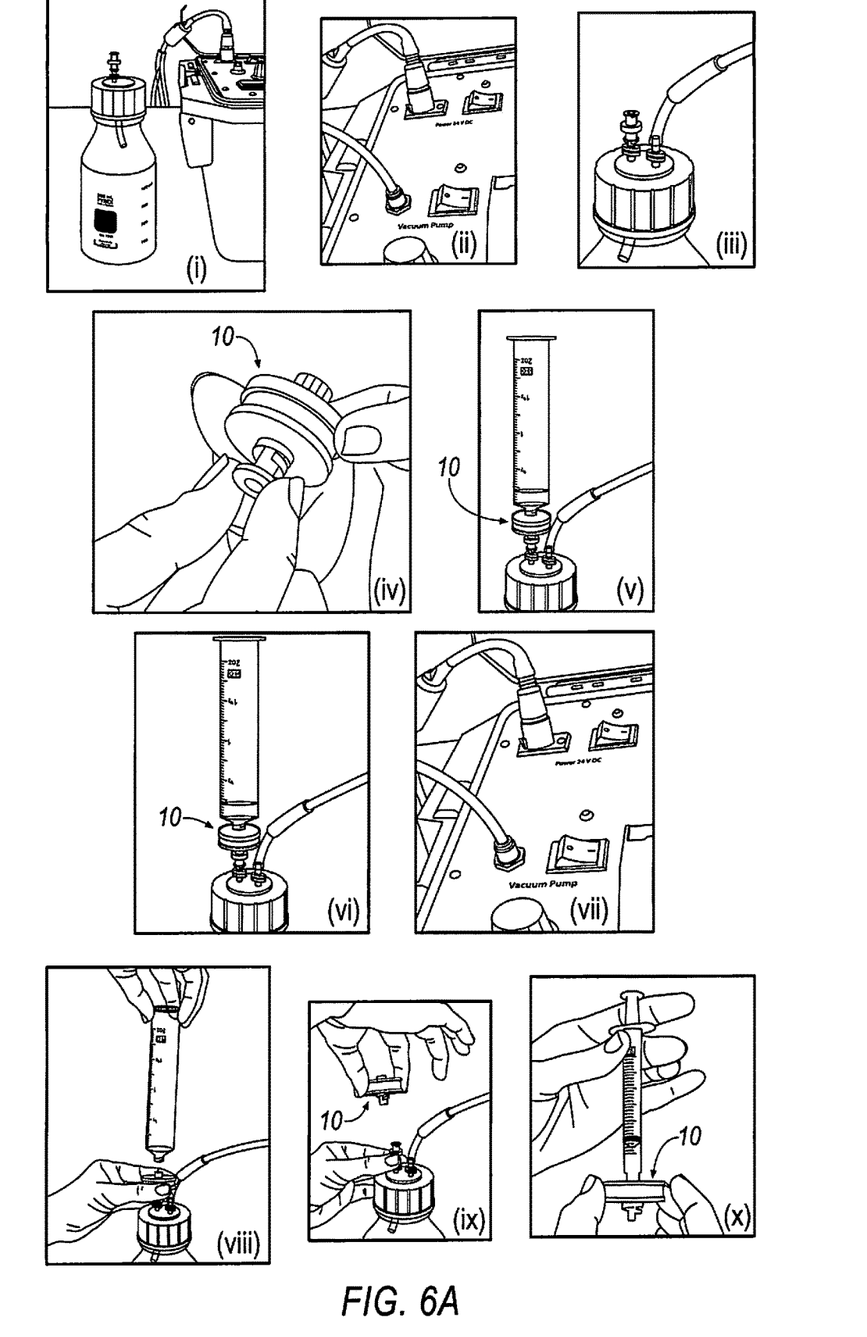
FIGS. 6A-D present an example protocol for carrying out an embodiment of a method for isolating single-stranded DNA from a sample containing cells.
Figure 6B:
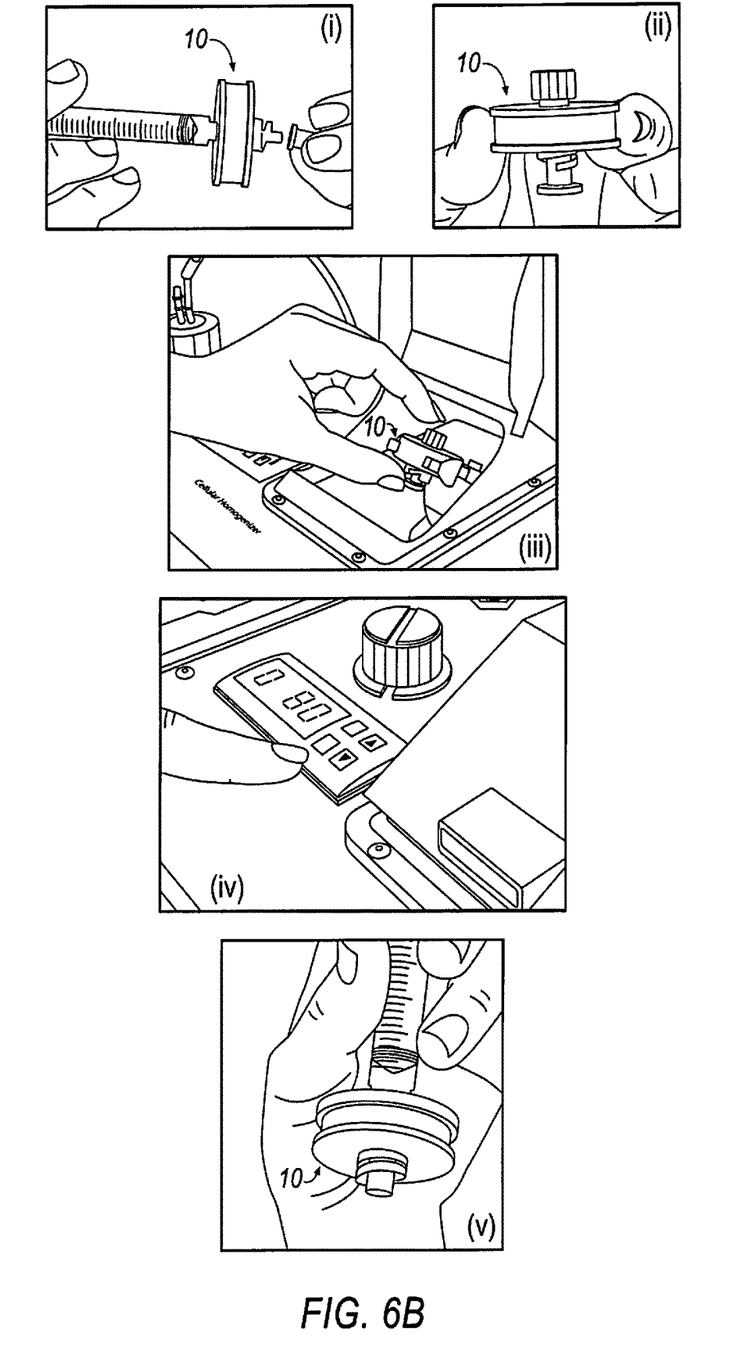
Figure 6C:
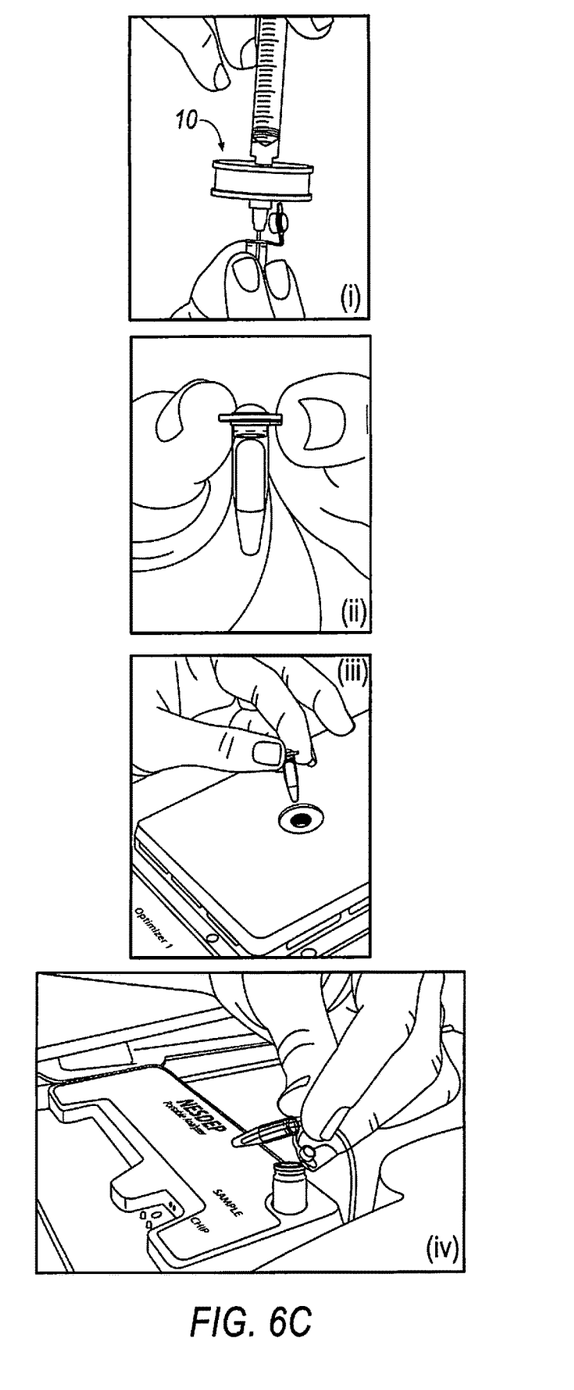
Figure 6D:
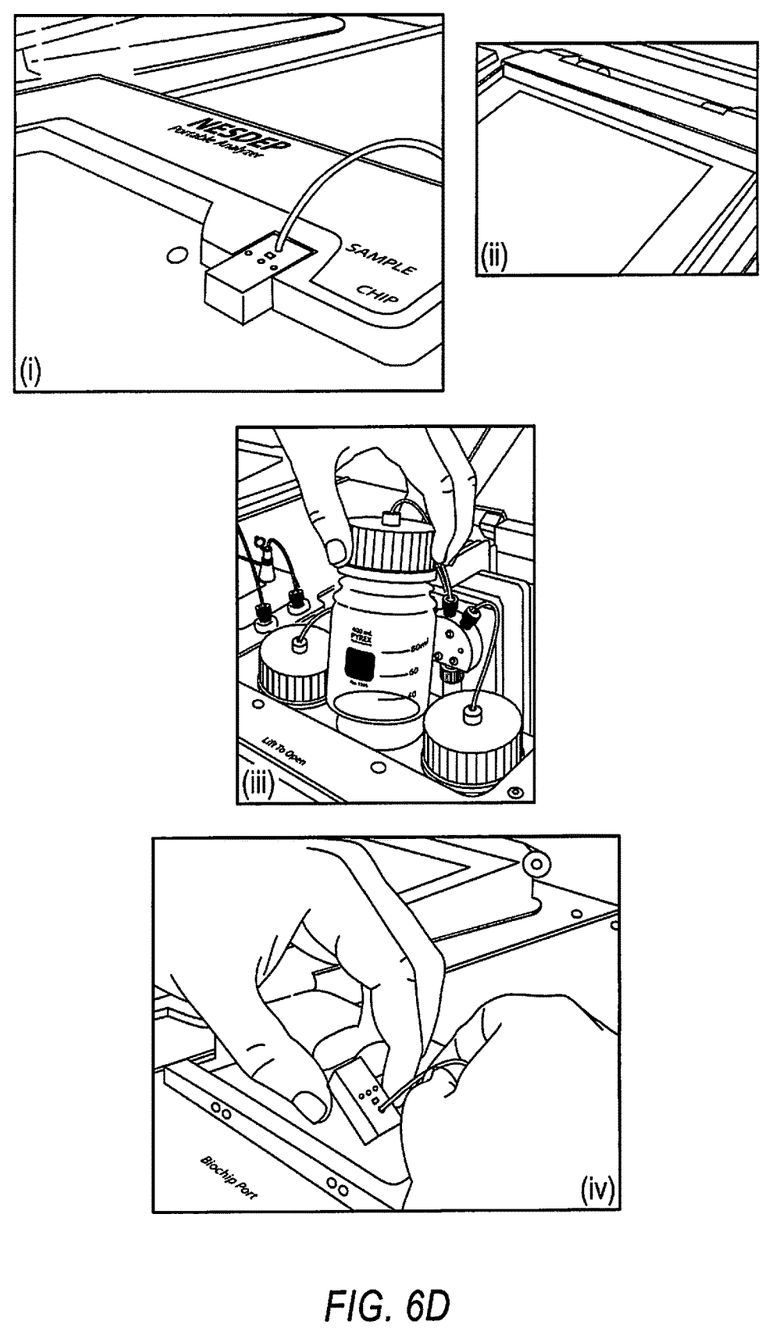

The sample is removed from the optimizer and placed in a sample vial holder. See FIG. 6C(iv). The sample vial holder is equipped with a magnet to attract magnetic substrate 52 (bound to dsDNA) and hold magnetic substrate 52 at the bottom of the sample vial. The liquid (containing ssDNA) is then withdrawn from the sample vial and sent to downstream applications, such as a DNA biochip detection assay. 6D(i)-6D(iv).

Example No. 2: Method of Manufacture

With reference to FIG. 7, an example of a method of manufacture of cartridge 10 is described. Cartridge 10 is assembled from multiple components (from top to bottom): a luer cap 31, top piece 32 ("top SPC" or "top sample prep cartridge"), particulate material 20 (glass beads), membrane 12, bottom piece 34 ("bottom SPC" or "bottom sample prep cartridge"), and a luer plug 33.

Luer cap 31 and luer plug 33 are commercially available and configured to attach to standard luer fittings at entrance port 16 and exit port 18 of the top SPC 32 and bottom SPC 34. Luer cap 31 and Luer plug 33 hold contents within cartridge 10. 0.3 grams of particulate material 20 (glass beads) are weighed and loaded in cartridge 10.

Membrane 12 is held in place by the connection between top SPC 32 and bottom SPC 34.

Top SPC 32 and bottom SPC 34 are made from plastic. Cartridge 10 is designed to accept up to 100 mL of liquid. Top SPC 32 and bottom SPC 34 are sonic-welded together and fix membrane 12 in place. Top SPC 32 and bottom SPC 34 have an entrance port 16 and an exit port 18, respectively, with standard luer lock fittings. Top SPC 32 and bottom SPC 34 are made using three dimensional printing. Bottom SPC 34 includes contains channels 14 in the form of a matrix. The channel matrix is made using three dimensional printing for bottom SPC 34 configured to form bottom SPC with a plurality of channels 14.

For assembly, membrane 12 is inserted into bottom SPC 34, top SPC 32 is inserted into bottom SPC 34, the components are sonic welded together, luer plug 33 is attached to bottom SPC 34, particulate material 20 is inserted into top SPC 32 through the entrance port 16, and luer cap 31 is attached.

Example No. 3: Cartridge Embodiment

With reference to FIGS. 8A-C and 9A-B an example of an embodiment of cartridge 10 is shown. FIGS. 8A-C and 9A-B show the architecture of an example of top SPC 32 and bottom SPC 34, respectively, as described herein. Top SPC 32 and bottom SPC 34 may be sonic welded together to form cartridge 10.

Figures 8A, 8B:
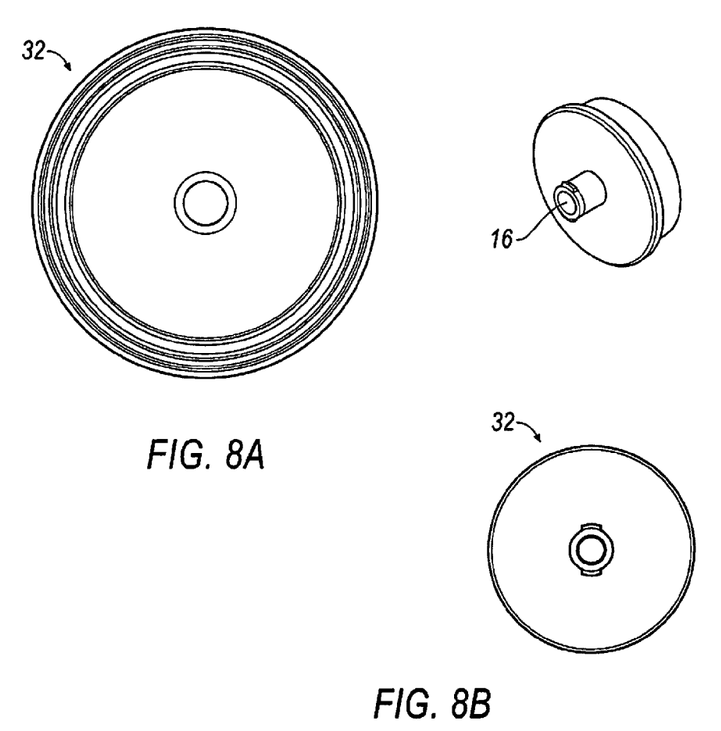
FIGS. 8A-C present an illustration of an embodiment of an top piece of a cartridge (e.g., a top SPC).
Figure 8C:
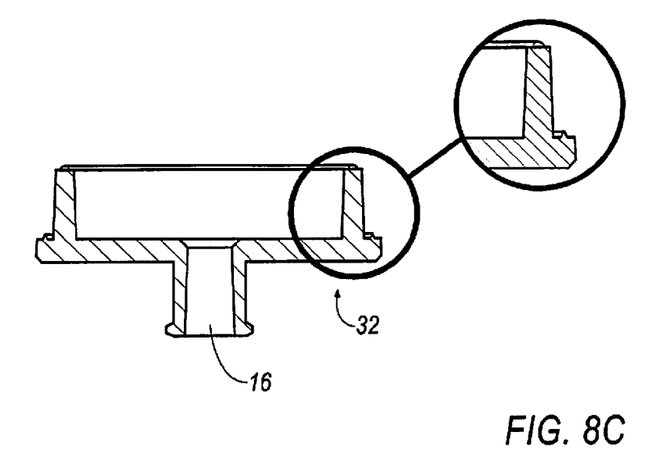

With reference to FIGS. 8A-C, top SPC 32 has a cylindrical shape with a top surface, an entrance port 16 having standard luer lock fittings 17 extending from the center of the top surface, and side wall extending downward from the edge of the top surface.

Figure 9A:
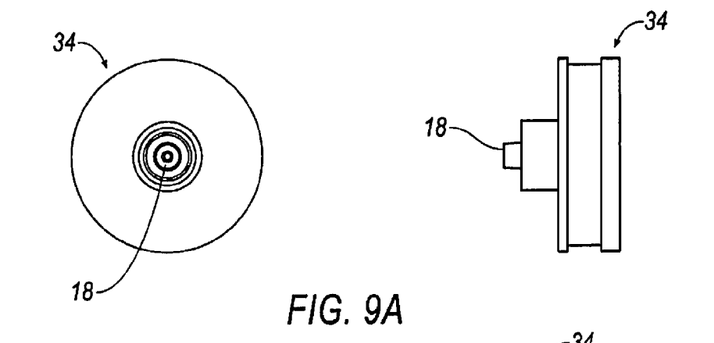
FIGS. 9A-B present an illustration of an embodiment of a bottom piece of a cartridge (e.g. a bottom SPC).
Figure 9B:
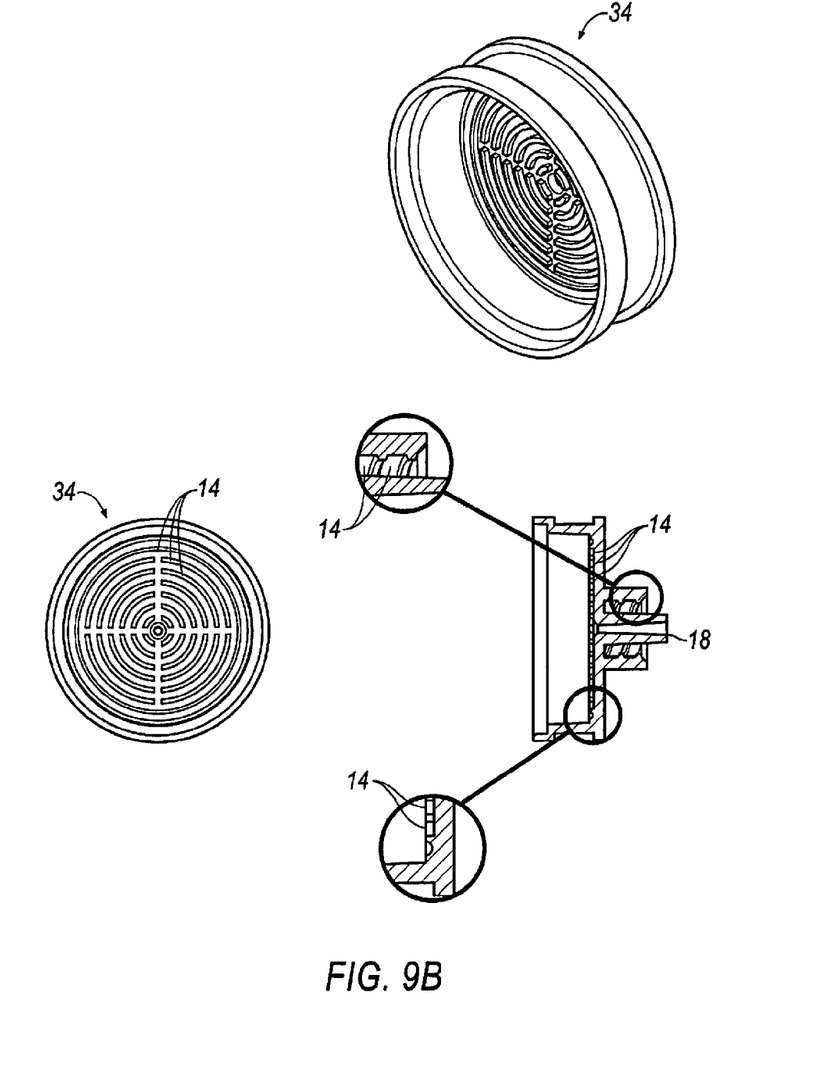

With reference to FIGS. 9A-B, bottom SPC 34 has a cylindrical shape with a bottom surface, an exit port 18 having standard luer lock fittings 19 extending from the center of the bottom surface and side walls extending upward from the edge of the top surface. Further a plurality of channels 14 are formed within bottom SPC 34. Channels 14 form a pattern extending radially outward from the center of bottom SPC 34.

Example No. 4: E. coli Test

Figure 10:
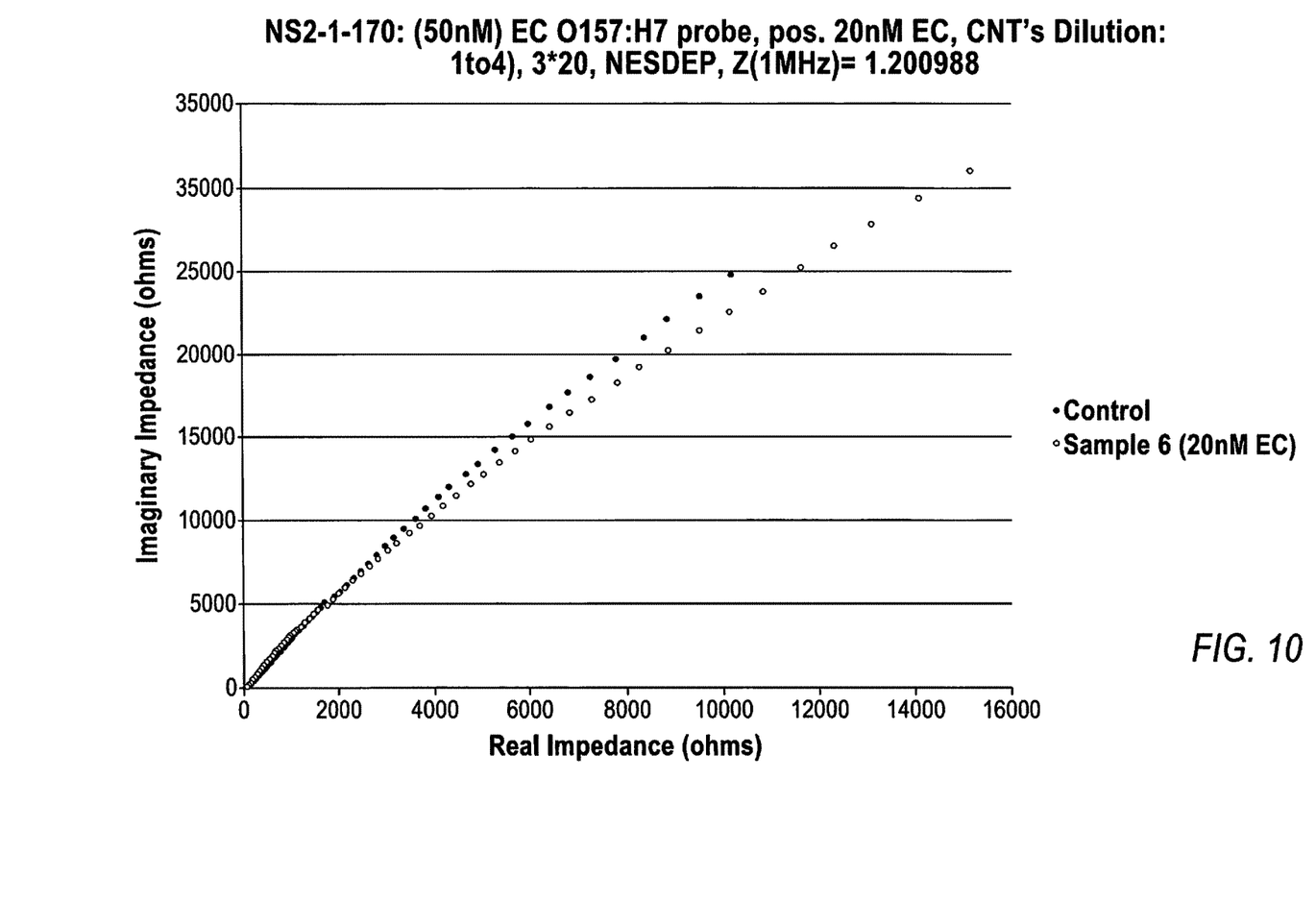
FIG. 10 presents an illustration of a graph of real impedance versus the imaginary impedance for an exemplary electrochemical detection assay using isolated ssDNA.

A variety of ground beef samples were tested using the F Cubed NESDEP IU (FIG. 5) and benchmark plate cultures. The pathogen E. coli 0157:H7 was inoculated into ground beef samples. The sample concentration was $10^2$ cells per mL. The sample was processed as described in the process protocol of Example No. 1. The isolated ssDNA sample then underwent detection using an electrochemical detection assay. An example of impedance data generated from an electrochemical detection assay is shown in FIG. 10. Sensitivity, specificity, negative predictive value, and positive predictive value were all 100%. Results are shown in Table 1.

TABLE 1

| | E. coli test results | | | | | |
|---|---|---|---|---|---|---|
| SITE ID[1] | F3 SAMPLE NUMBER[2] | ASSAY RESULT[3] | PLATE RESULT[4] | SAMPLE TYPE[5] | ASSAY PROCESS[6] | NOTES |
| A | 1 | Positive | Yes | 75% | Q | 1.5 CFU Index = 1.11 |
| A | 2 | Positive | Yes | 75% | Q | 5.0 CFU Index = 1.20 |

TABLE 1-continued

E. coli test results

| SITE ID[1] | SAMPLE NUMBER[2] | F3 ASSAY RESULT[3] | PLATE RESULT[4] | SAMPLE TYPE[5] | ASSAY PROCESS[6] | NOTES |
|---|---|---|---|---|---|---|
| A | 3 | Positive | Yes | 75% | Q | 15.0 CFU Index = 1.35 |
| A | 4 | Positive | Yes | 50% | Q | 1.5 CFU Index = 1.11 |
| A | 5 | Positive | Yes | 50% | Q | 5.0 CFU Index = 1.03 |
| A | 6 | Positive | Yes | 50% | Q | 15.0 CFU Index = 1.20 |
| A | 7 | Negative | No | 75% | Q | 5.0 CFU Index = 0.01 |
| A | 8 | Positive | Yes | 75% | Q | 15.0 CFU Index = 1.35 |
| A | 9 | Negative | No | 50% | Q | 1.5 CFU Index = 0.87 |
| A | 10 | Positive | Yes | 50% | Q | 5.0 CFU Index = 1.13 |

LEGEND
[1](A) F3 Labs/(B) Off-site/(C) Undefined
[2]F3 Number Sequence
[3]F3 NESDEP IU System
[4]Plate culture With Manual Smear and Incubate
[5]Samples Obtained From Martin'S Supermarkets (50% GB Or 75% GB)
[6](Q) Qualitative F3 NESDEP/(F) Quantitative F3 NESDEP Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for isolating DNA from a sample containing cells, comprising
   a cartridge having an entrance port and an exit port;
   a membrane disposed between the entrance port and the exit port;
   a plurality of channels between the membrane and the exit port; and
   a plurality of particulate material configured to mechanically lyse cells, wherein the plurality of particulate material is located between the membrane and the entrance port.

2. The device of claim 1, wherein the channels are adjacent to the membrane.

3. The device of claim 1, wherein each of the channels has a channel entrance, a channel exit, and a channel wall, wherein the channel entrance is adjacent to the membrane.

4. The device of claim 3, wherein the channel entrance has a length and width, wherein the length is about 0.1 mm to about 100 mm and the width is about 0.1 mm to about 10 mm.

5. The device of claim 1, having from about 2 to about 1000 channels.

6. The device of claim 1, wherein the channels are arranged in a matrix.

7. The device of claim 6, wherein the channels are adjacent to each other.

8. The device of claim 6, wherein the channels are spaced apart from each other.

9. The device of claim 8, further comprising a solid barrier between each channel entrance.

10. The device of claim 1, wherein the membrane is configured to be permeable to DNA but substantially impermeable to cells.

11. The device of claim 1, wherein the membrane is configured to be permeable to DNA but substantially impermeable to non-DNA cellular material.

12. The device of claim 1, wherein the membrane comprises a cellulose material.

13. The device of claim 1, wherein the membrane has pores.

14. The device of claim 13, wherein the pores are from about 10 nm to 1 micron in diameter.

15. The device of claim 1, wherein the particulate material comprises glass or stainless steel.

16. The device of claim 1, wherein the particulate material comprises a plurality of microbeads.

17. The device of claim 16, wherein the microbeads have a diameter of from about 1 micron to about 1000 microns.

18. The device of claim 1, wherein the entrance port and exit port comprise standard luer lock fittings.

19. The device of claim 1, wherein the cartridge includes a bottom piece that supports the membrane and the plurality of channels are formed from cavities in the bottom piece of the cartridge.

20. A system for isolating DNA from a sample containing cells comprising the device of claim 1, and a vacuum to pull fluid into the cartridge.

21. The system of claim 20, further comprising a cellular homogenizer to shake the cartridge.

22. The system of claim 21, wherein the cellular homogenizer is capable of shaking the cartridge at a rate of up to 5000 rpm.

23. The system of claim 21, further comprising a thermal cycler configured to subject the DNA to thermal cycling for a polymerase chain reaction (PCR).

24. The system of claim 23, further comprising a magnetic substrate wherein the magnetic substrate is a coating with a binding affinity for double-stranded DNA.

25. The system of claim 24, further comprising a magnet configured to apply a magnetic field to the magnetic substrate.

26. The system of claim 24, wherein the magnetic substrate is a plurality of magnetic beads.

27. A method of processing DNA from a sample, comprising
   providing a sample containing cells having DNA;
   transferring the sample into the device of claim 1;
   lysing the cells to release the DNA and non-DNA cellular material;
   passing the DNA through the membrane; and
   passing the DNA through the channels;
   wherein the DNA is isolated from the sample.

28. The method of claim 27, wherein the sample comprises blood, exudate, water, or food.

29. The method of claim 27, wherein the transferring comprises using a vacuum to transfer the sample into the cartridge.

30. The method of claim 27, wherein the mechanical lysing substantially destroys the non-DNA cellular material.

31. The method of claim 27, wherein greater than 50%, 60%, 70%, 80%, 90%, 95%, or 99% of the non-DNA cellular material in the sample does not pass through the membrane.

32. The method of claim 27, wherein greater than 50%, 60%, 70%, 80%, 90%, 95%, or 99% of the DNA in the sample is passed through the membrane and the channels.

33. The method of claim 27, further comprising transferring the isolated DNA to a DNA amplification chamber and amplifying the isolated DNA by a polymerase chain reaction (PCR), wherein the PCR is asymmetric, to produce double-stranded DNA and single-stranded DNA.

34. The method of claim 33, wherein a portion of the single-stranded DNA is within a specified range of lengths.

35. The method of claim 33, further comprising binding the double-stranded DNA to a magnetic substrate and applying a magnetic field to the substrate, wherein the magnetic field attracts the substrate bound to the double-stranded DNA, and isolating the single-stranded DNA.

* * * * *